United States Patent [19]

Marquis et al.

[11] 4,052,456

[45] Oct. 4, 1977

[54] METHOD OF PREPARING POLYAMINOPOLYPHENYLMETHANES

[75] Inventors: Edward T. Marquis; Lewis W. Watts, Jr., both of Austin, Tex.

[73] Assignee: Texaco Development Corporation, New York, N.Y.

[21] Appl. No.: 763,967

[22] Filed: Jan. 31, 1977

[51] Int. Cl.² .............................................. C07C 85/08
[52] U.S. Cl. .......................... 260/570 D; 260/570.5 P; 260/570.9
[58] Field of Search ................................... 260/570 D

[56] References Cited

U.S. PATENT DOCUMENTS 3,676,497   7/1972   Reechin et al. .................... 260/570

Primary Examiner—Robert V. Hines
Attorney, Agent, or Firm—Carl G. Ries; Thomas H. Whaley; James L. Bailey

[57] ABSTRACT

Covers a method of preparing diaminodiphenylmethanes and higher homologues thereof which comprises the step of condensing aniline and formaldehyde in the presence of an aluminum silicide catalyst.

3 Claims, No Drawings

METHOD OF PREPARING POLYAMINOPOLYPHENYLMETHANES

BACKGROUND OF THE INVENTION

1. Field of the Invention

This invention relates to the field of polyamines.

2. Description of the Prior Art

The process of producing aromatic polyamines by the reaction of aniline and formaldehyde is well known and described for example in U.S. Pat. Nos. 2,683,730; 3,277,173; 3,344,162; and 3,362,979. By phosgenating these amines the corresponding isocyanates are obtained. The polyamines produced by the condensation of aniline and formaldehyde usually consist of a mixture of poly(methylenephenylamines) of functionality greater than two and the 2,2', 2,4' and 4,4' isomers of diaminodiphenylmethane. By reaction with phosgene a corresponding mixture of polyisocyanates and diisocyanates is prepared which is useful in producing, for example, polyurethane foam.

One mode of reacting aniline with formaldehyde is to effect this reaction in the presence of a strong mineral acid, such as hydrochloric acid. Here a reaction occurs between the corresponding aniline hydrochloride and formaldehyde to provide a reaction mixture which, upon neutralization with a base, may be treated to recover the polyphenylamines. This process has left much to be desired. For example, it is necessary to utilize large quantities of both a mineral acid and a base which adversely affect the economics of the process and also the ease of conducting the reaction. In addition, the use of large quantities of mineral acids and bases presents a severe corrosion problem. Also, the inorganic salt formed poses environmental difficulties with respect to disposal and/or recovery.

As an improvement to the conventional mineral acid catalyzed aniline-formaldehyde condensation see of a solid acidic siliceous catalyst has been proposed (see U.S. Pat. No. 3,362,979). This is economically favorable over the conventional hydrochloric acid catalyzed process since use of large quantities of corrosive acid and caustic are avoided. However, even this process has some drawbacks, particularly, in that the rate of reaction is not as paid as desired and rearrangement of produce amines at conventional conditions is not considered sufficiently complete.

SUMMARY OF THE INVENTION

The invention relates to a process for making aromatic polyamines by the reaction of aniline and formaldehyde in the presence of an aluminum silicide catalyst.

DESCRIPTION OF THE PREFERRED EMBODIMENT

A method of preparing diaminodiphenylmethane and higher homologues thereof has now been discovered. The invention comprises the step of condensing aniline and formaldehyde in the presence of an aluminum silicide catalyst. A mixture of products is produced which includes the diaminodiphenylmethane isomers comprising the 2,2', 2,2', and 4,' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables the proportions of diamines, and higher polyamines present in the final reaction mixture may be widely varied. However, usually the reaction mixture contains 20–80 percent by weight of diamine with the remainder being higher polyamines thereof. More often the percentage of diamines in the mixture is 30–70 percent and most often ranges from about 35 to about 55 weight percent. Correspondingly the polymeric products higher than the dimer products usually in the preferred embodiment range from the 30 to 70 percent by weight, and most often range from about 45 to about 65 percent by weight. With respect to product distribution of the dimer usually 1–10 percent by weight of total dimer is the 2,2' isomer, with the remainder being 2,4' and 4,4' isomers. Most often the content of dimer is 1–5 percent 2,2' isomer with the remainder, or 95–99 percent being 2,4' and 4,4' isomers, based on total dimer content. Generally the higher molecular weight polymethylene polyphenylpolyamines have an average functionality of from about 2.1 to about 3.0, more often 2.2–2.7.

The aluminum silicide catalyst is a known material which is prepared by reacting aluminum with silicon. The resultant composition is similar to an inter-metallic compound, thus generally exhibiting many of the physical properties of pure metals. Normal valence rules do not generally apply to silicide formation. The aluminum silicide may be prepared via a number of routes. These include direct combination of the aluminum and silicon elements, reduction of aluminum oxide with silicon, reaction of aluminum with silica in the presence of carbon, and reduction of the oxide with a number of materials such as magnesium or aluminum in presence of silica and silicon.

One commercially available aluminum silicide has the formula AlS, with a formula weight of 55.07. Analysis of the material used 49.0% Si and 50% Al.

The amount of catalyst used here may be varied according to the choice of the experimenter. Usually, however, 0.5–3.0 percent by weight of catalyst based on weight on aniline is employed. More often, the amount of catalyst utilized is 1–2 percent by weight based on aniline weight.

In order to prepare the methylene-bridged polyphenyl polyamines (term includes both diaminodiphenylmethane isomers and higher homologues thereof or higher polymers) the following process conditions are preferred.

The molar ratio of aniline to formaldehyde may be varied within comparatively wide limits. Thus, for example, from about 1 to about 10 mols of aniline may be employed per mol of formaldehyde. In general, at the lower aniline:HCHO ratios, such as ratios of from about 1:1 to about 2.5:1, the higher polymers will be formed preferentially and the yield of higher polymers is in excess of the yield of dimer. However, as progressively larger amounts of aniline are used, the yield of dimer is progressively increased at the expense of polymer yield. Thus, with aniline to formaldehyde ratios of from about 3:1 to about 10:1 or more, the reaction product will be composed primarily of the dimer. As indicated above, the dimer will be formed as a mixture of the 2,4'- and 4,4'- diamine isomers.

Formaldehyde may be employed in any of its commercially available forms. Thus, formalin, paraformaldehyde, "stabilized" methanol solutions of formaldehyde, etc., may be employed.

The reaction may be conducted in the presence or absence of a solvent. When a solvent is to be employed, it may be any of the conventionally known hydrocarbon solvents or chlorinated hydrocarbons, such as aromatic or aliphatic solvents boiling within the range from about 100° to about 200° C. The solvent should be employed in an amount sufficient to provide a single phase solution of the amine compound.

The reaction conditions to be employed may suitably include a reaction temperature within the range of about 100° to about 300° C, and more preferably within the range of about 150° to about 250° C.

Pressure is not particularly critical with respect to the process. However, the pressure should be sufficient to provide for liquid phase reaction conditions. Thus, pressures ranging from atmospheric up to 1000 psig may be employed.

The reaction proceeds smoothly under the above-described conditions, and is normally substantially complete upon addition of the formaldehyde. However, because of the exothermic nature of the reaction, it is normally preferable to add the formaldehyde at a rate such that the desired reaction temperature can be maintained. It is normally possible to bring the reaction to completion within from about 5 minutes to about 8 hours in conventional equipment. More often the reaction is complete in ¼–4 hours.

The polyaminopolyphenylmethanes of the present invention are recovered from the reaction mixture by any desired means. They are conveniently recovered by filtering the catalyst and removing water and excess aniline under reduced pressure. The bottoms from these operations will consist of diamine and polyamine in proportions depending on the ratio of aniline to for formaldehyde, as indicated above. If it is desired to separate the diamine from the polyamine, that is easily accomplished by simple distillation whereby the diamine is flashed from the nonvolatile polyamine residue. The overhead product may be removed, for example, at from about 170° C to about 200° C at about 0.5 to about 0.025 mm. Hg pressure and will consist essentially of diaminodiphenylmethane.

The dimer and higher products of the present invention are useful for a variety of purposes. For example, they may be utilized as raw materials for the production of the corresponding polyisocyanates, or used as such as epoxy curing agents.

The advantages in using an aluminum silicide catalyst in the process of the invention are many and varied. In the first place a more substantially rearranged product is achieved in a desirable manner, compared to many prior art catalyst used in this process. In addition, many commonly used catalysts such as hydrochloric acid are highly corrosive, whereas there is no indication here that the catalysts used here are corrosive in any manner. Again, it has been found that the aluminum silicides are considerably more active than other known catalysts such as silica-alumina, which latter catalyst does, however, avoid the discussed problems of corrosion. Again, only small amounts of catalyst need be employed and the catalyst is readily removed from the reaction mixture by filtration. Surprisingly, relatively complete rearrangement of product amine occurs at conditions which, with silica-alumina catalyst, do not afford a suitable product.

The following examples illustrate the process of the invention. It is understood, of course, that these examples are merely illustrative, and that the invention is not to be limited thereto.

EXAMPLE I

Aniline (186.0 g, 2.0 moles), formaldehyde (30.0 g, 1.0 mole) and 1.9 g (or 1% by wt. basis aniline) aluminum silicide (AlSi, available from Ventron Corp.) were added to a 1—1. ss stirred autoclave. The clave was flushed with $N_2$. (The formaldehyde was added in the form of formalin or a 37% aqueous solution of formaldehyde.) The mixture was heated to 200° C at autogenous pressure and held there for 1 hour. The crude mixture was cooled, stripped of water and filtered. The crude amine was examined by NMR and found to contain only 8% N-benzyl secondary amine and some 9% n-methyl secondary amine. In a noncatalyzed run (Example II below) we observed some 33% N-benzyl secondary amine and 23% aminal type secondary amine or a total of some 55% unrearranged material vs. only 8% using aluminum silicide (under identical reaction conditions). Further, in a run exactly similar except silica alumina catalyst was used (Example III below), we observed some 12.1% N-benzyl secondary amine.

EXAMPLE II

To a stirred 1—1. ss clave was added aniline (372 g, 4.0 moles and formaldehyde (2.0 moles, 60.0 g) and the clave was flushed with $N_2$ and heated to 200° C at autogenous pressure and held there for 1 hour stirring. The reactor effluent was stripped of $H_2O$ and an NMR spectrum obtained on the crude amine indicating the presence of some 23% animal type, $\phi NH$—$CH_2$—$NH\phi$, secondary amine, and some 33% N-benzyl secondary amine. Further, the N-methyl secondary amine content was 14.5%.

EXAMPLE III

To a stirred 1—1. ss clave as added aniline (372 g, 4.0 moles, ) formaldehyde (60.0 g, 2.0 moles) and silica alumina (3.7 g, 1.0% by wt. basis aniline charged). The clave was flushed with $N_2$ and heated to 200° C at autogenous pressure and held there for 1 hr. The reactor effluent was stripped of water, filtered, and the aniline stripped. The product amine still contained some 12.1% N-benzyl secondary amine (unrearranged) by NMR spectroscopy, and 6.1% N-methyl secondary amine.

We claim:

1. A method of preparing diaminodiphenylmethane and higher homologues thereof which comprises the step of condensing aniline and formaldehyde in the presence of an aluminum silicide catalyst.

2. The method of claim 1 wherein said catalyst is present in an amount ranging from about 0.5 to about 3.0 percent by weight based on the weight of aniline present.

3. The method of claim 2 wherein said catalyst present in an amount of 1–2 percent by weight.

* * * * *